United States Patent
Lee et al.

(10) Patent No.: US 9,678,048 B2
(45) Date of Patent: Jun. 13, 2017

(54) METHOD OF EVALUATING FINAL EQUILIBRIUM PH OF CONTAMINATED SOIL ON SITE BY USING PASTE PH

(71) Applicant: KOREA INSTITUTE OF GEOSCIENCE AND MINERAL RESOURCES, Daejeon (KR)

(72) Inventors: Pyeong-Koo Lee, Daejeon (KR); Jung-Hae Choi, Daejeon (KR)

(73) Assignee: KOREA INSTITUTE OF GEOSCIENCE AND MINERAL RESOURCES, Daejeon (KR)

( * ) Notice: Subject to any disclaimer, the term of this patent is extended or adjusted under 35 U.S.C. 154(b) by 636 days.

(21) Appl. No.: 14/181,312

(22) Filed: Feb. 14, 2014

(65) Prior Publication Data

US 2014/0288833 A1 Sep. 25, 2014

(30) Foreign Application Priority Data

Mar. 25, 2013 (KR) ........................ 10-2013-0031318

(51) Int. Cl.
*G01N 33/24* (2006.01)
*G01N 31/22* (2006.01)

(52) U.S. Cl.
CPC ........... *G01N 31/221* (2013.01); *G01N 33/24* (2013.01)

(58) Field of Classification Search
CPC ........ A01N 59/00; A01N 25/02; C11D 3/044; C02F 1/66; C02F 2209/06; B09C 1/002; G01N 33/24; G01N 31/221
See application file for complete search history.

(56) References Cited

U.S. PATENT DOCUMENTS

| | | | |
|---|---|---|---|
| 2,178,550 A * | 11/1939 | Acree ................. | G01N 31/221 422/76 |
| 5,172,332 A * | 12/1992 | Hungerford ............. | E03F 7/00 700/267 |
| 6,356,830 B1 | 3/2002 | Adamchuck et al. | |
| 7,679,058 B2 * | 3/2010 | Kissel ................. | G01N 21/274 250/339.07 |
| 8,834,725 B2 * | 9/2014 | Bhaduri ................ | C02F 1/5236 210/513 |

(Continued)

FOREIGN PATENT DOCUMENTS

| | | |
|---|---|---|
| JP | 2000055909 A | 2/2000 |
| JP | 2009061420 A | 3/2009 |

(Continued)

*Primary Examiner* — Toan Le
*Assistant Examiner* — Jeffrey Aiello
(74) *Attorney, Agent, or Firm* — Lewis Roca Rothgerber Christie LLP

(57) ABSTRACT

Disclosed is a method of evaluating a final equilibrium pH of a contaminated soil on site by using a paste pH. The method includes measuring the paste pH by adding a solution to the contaminated soil, and evaluating the final equilibrium pH according to an initial pH by applying the paste pH to $$\text{Final equilibrium pH} = (\text{paste pH} + 1) \times \exp\left(-\frac{1}{\text{initial pH}}\right) - \exp\left(-\frac{1(\text{paste pH} + 1)}{\text{initital pH}}\right), \quad \text{Equation 1}$$

in which the initial pH is a predetermined integer in a range of 1 to 10.

3 Claims, 2 Drawing Sheets

(56) References Cited

U.S. PATENT DOCUMENTS

| | | | |
|---|---|---|---|
| 2006/0185411 A1* | 8/2006 | Hojjatie | C05D 3/00 71/31 |
| 2007/0092407 A1* | 4/2007 | Xiao | B01L 3/50273 422/82.05 |
| 2008/0137069 A1* | 6/2008 | Kissel | G01N 21/274 356/72 |
| 2008/0179253 A1* | 7/2008 | Clark | B01J 20/06 210/660 |
| 2009/0311048 A1* | 12/2009 | Horst | C02F 1/52 405/128.5 |
| 2010/0176061 A1* | 7/2010 | Monzyk | B01D 21/01 210/702 |
| 2011/0139695 A1* | 6/2011 | Borden | B09C 1/002 210/170.07 |
| 2012/0053427 A1* | 3/2012 | Markle | A61B 5/1459 600/301 |
| 2012/0228229 A1* | 9/2012 | Douglas | C01F 7/005 210/662 |
| 2015/0196708 A1* | 7/2015 | Mason | A61M 5/172 604/66 |

FOREIGN PATENT DOCUMENTS

| | | |
|---|---|---|
| KR | 10-0571601 | 1/2005 |
| KR | 20120080274 A | 7/2012 |

\* cited by examiner

METHOD OF EVALUATING FINAL EQUILIBRIUM PH OF CONTAMINATED SOIL ON SITE BY USING PASTE PH

CROSS-REFERENCE TO RELATED APPLICATION

This application claims priority to Korean Patent Application No. 10-2013-0031318 filed on Mar. 25, 2013, and all the benefits accruing therefrom under 35 U.S.C. §119, the contents of which is incorporated by reference in its entirety.

BACKGROUND OF THE INVENTION

1) Field of the Invention

The present invention relates to a method of evaluating a final equilibrium pH of a contaminated soil on site by using a paste pH.

2) Background of Related Art

In Korea, thousands of abandoned metal mines are scattered and mineral tailings and waste rocks discharged from the abandoned metal mines are neglected in many areas of the abandoned metal mines. Acid drainage and dissolved metal are discharged from the mineral tailings and the waste rocks to surroundings, thereby cause severe damage to the surrounding ecosystem of the abandoned mines and the health of a human being. Accordingly, the priority for rapid and effective contamination evaluation processes of the mineral tailings or the waste rocks discharged from the abandoned mines must be immediately determined.

In order to evaluate the contamination degree of a soil contaminated with mineral tailings or the waste rocks, the collection of the representative sample of the mineral tailings or the waste rocks piled up in the abandoned metal mine is important. In other words, standards must be established with respect to a scheme of reasonably and systematically collecting samples according to the characteristics (deposits type, mineral type, ground, or the like) of the mineral tailings or the waste rocks and to the number of samples.

Most domestic abandoned mines are distributed in mountainous territories difficult to access thereto, so that samples may not be easily investigated, collected, and moved. Accordingly, much time is spent to collect samples of the mineral tailings discharged from many abandoned metal mines distributed all over the country. In addition, as the number of collected mineral tailings is increased, the information of representative heavy metal of the mineral tailings exerting an influence on contamination may be more acquired. However, when an excess amount of samples are analyzed, much time and cost are required. Accordingly, a method of economically and rapidly evaluating a soil contaminated by the abandoned metal mine is required.

As a related art of the present invention, there is Korea Patent Registration No. 10-0571601 titled "BIOLOGICAL METHOD FOR CUT OFFING AND PURIFYING CONTAMINATED SOIL" (issued on Apr. 1, 2006).

SUMMARY OF THE INVENTION

The present invention a method of evaluating a final equilibrium pH of a contaminated soil on site by using a paste pH, capable of estimating the final equilibrium pH on site in real time by evaluating the pH of the contaminated soil around a wasted mine and an area to produce heavy metal.

Another object of the present invention is to exactly specify an artificial contamination source of a Pb isotope resulting from the industrial activity of a human being.

In order to accomplish the above object, there is provided a method of evaluating a final equilibrium pH of a contaminated soil on site by using a paste pH. The method includes measuring the paste pH by adding a solution to the contaminated soil, and evaluating the final equilibrium pH according to an initial pH by applying the paste pH to Equation 1, $$\text{Final equilibrium pH} = (\text{paste pH} + 1) \times \exp\left(-\frac{1}{\text{initial pH}}\right) - \exp\left(-\frac{1(\text{paste pH} + 1)}{\text{initital pH}}\right), \quad \text{Equation 1}$$

in which the initial pH is a predetermined integer in a range of 1 to 10.

As described above, according to the present invention, the final equilibrium pH can be evaluated on site in real time by using the pH of the contaminated soil, so that the contaminated soil can be analyzed in real time and the contamination degree can be estimated. In addition, since the final equilibrium pH of the contaminated soil can be found in real time, the time and the experimental cost can be reduced. Accordingly, the soil analysis can be effectively performed on site.

DETAILED DESCRIPTION OF THE INVENTION

Hereinafter, embodiments of the present invention will be described in detail with reference to accompanying drawings.

The advantages, the features, and schemes of achieving the advantages and features of the present invention will be apparently comprehended by those skilled in the art based on the embodiments, which are detailed later in detail, together with accompanying drawings.

The present invention is not limited to the following embodiments but includes various applications and modifications. The embodiments will make the disclosure of the present invention complete, and allow those skilled in the art to completely comprehend the scope of the present invention. The present invention is only defined within the scope of accompanying claims In addition, the detailed descriptions of well-known techniques incorporated herein may be omitted when they make the subject matter rather unclear.

The present invention provides a method of evaluating a final equilibrium pH of a contaminated soil on site by using a paste pH including measuring a paste pH by adding a solution to the contaminated soil, and evaluating the final equilibrium pH according to an initial pH by applying the measured paste pH to following Equation 1.

$$\text{Final equilibrium pH} = \qquad \text{Equation 1}$$
$$(\text{paste pH} + 1) \times \exp\left(-\frac{1}{\text{initial pH}}\right) - \exp\left(-\frac{1(\text{paste pH} + 1)}{\text{initital pH}}\right)$$

In Equation 1, the initial pH is a predetermined integer in the range of 1 to 10.

According to the method of evaluating the final equilibrium pH of the contaminated soil on site by using the paste pH of the present invention, the final equilibrium pH can be evaluated on site in real time by using the pH of the contaminated soil, so that the contaminated soil can be analyzed in real time and the contamination degree can be estimated.

In addition, since the final equilibrium pH of the contaminated soil can be found in real time, the time and the experimental cost can be reduced. Accordingly, the soil analysis can be effectively performed on site.

Figure 1:
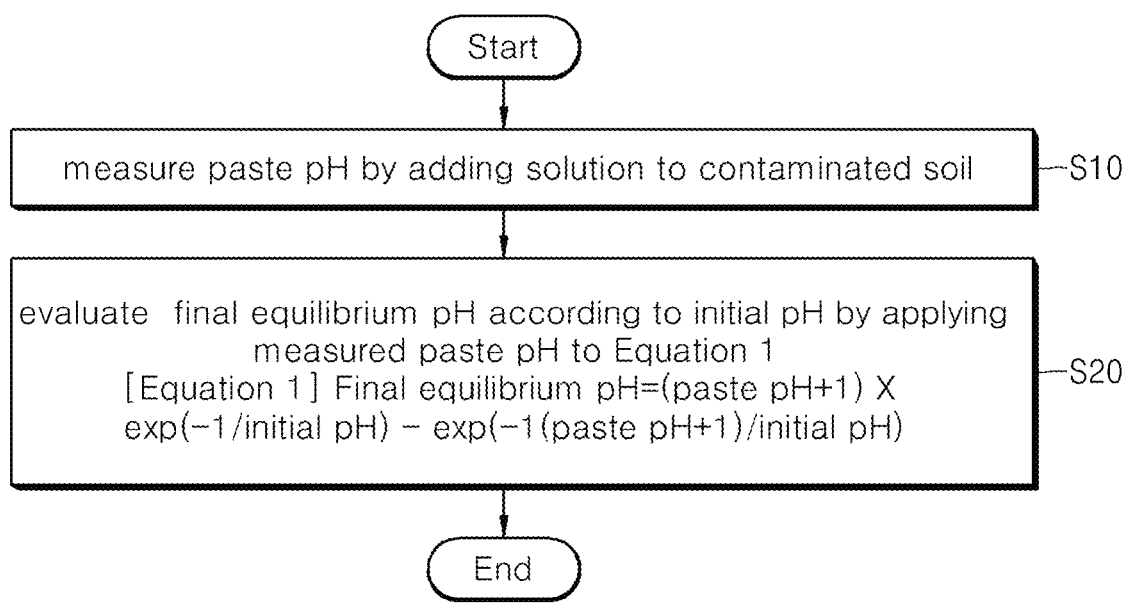
FIG. 1 is a flowchart showing a method of evaluating a final equilibrium pH of a contaminated soil on site by using a paste pH according to the present invention.

FIG. 1 is a flowchart showing the method of evaluating the final equilibrium pH of the contaminated soil on site by using the paste pH according to an exemplary embodiment of the present invention. Hereinafter, the present invention will be described in detail with reference to FIG. 1.

The method of evaluating the final equilibrium pH of the contaminated soil on site by using the paste pH according to the present invention includes measuring a paste pH by adding a solution to the contaminated soil (step S10).

The contaminated soil may include mineral tailings, or waste rocks, or both of the mineral tailings and the waste rocks. After the solution, in detail, distilled water or water is added to the contaminated soil to make the contaminated soil in a paste state, the paste pH is measured.

The method of evaluating the final equilibrium pH of the contaminated soil on site by using the paste pH according to the present invention includes evaluating the final equilibrium pH according to an initial pH in the range of 1 to 10 by applying the measured paste pH to following Equation 1 (step S20).

$$\text{Final equilibrium pH} = \qquad \text{Equation 1}$$
$$(\text{paste pH} + 1) \times \exp\left(-\frac{1}{\text{initial pH}}\right) - \exp\left(-\frac{1(\text{paste pH} + 1)}{\text{initital pH}}\right)$$

In Equation 1, the initial pH is a predetermined integer in the range of 1 to 10. In detail, the initial pH may be the pH of raindrop, underground water, or ore industry sewage.

Therefore, according to the method of evaluating the final equilibrium pH of the contaminated soil on site by using the paste pH of the present invention, after measuring the paste pH of the contaminated soil around the waste mine and the area to produce heavy metal, the final equilibrium pH can be evaluated on site in real time without analyzing the final equilibrium pH in a laboratory according to the pH of surrounding raindrop, underground water, or ore industry sewage, so that time and cost can be saved.

In order to ensure the reliability of the method of evaluating the final equilibrium pH of the contaminated soil on site by using the paste pH according to the present invention, following embodiments are provided regarding Korean representative mines such as Sangdong mine, Yeonhwa mine, Janggun mine, Samkwang mine, Deokchon mine, Sannae mine, Yeosu mine, Dokseong mine, Yaro mine, Taechang mine, Backwol mine, Gumgae mine, Munmyeong mine, Shinlim mine, Gakhee mine, Daeyang mine, Ilwall mine, and Jangja mine Hereinafter, Samkwang mine, which is one of representative mines, will be described as an example in detail. Samkwang mine is located in Sindaeri, Ungokmyeon, Cheongyanggun, Chungcheongnamdo, Korea. Samkwang mine is the biggest mine among domestic metal mines. In Samwang mine, gold and silver have been developed from Japanese occupation, and abandoned in 2001. Since 11 million tons of mineral tailings and several thousand tons of waste rocks are deposited, contamination is spread downward of the mine along a water system. Particularly, in Samkwang mine, the high content of arsenic (As) is contained in the mineral tailings and the soil around the mine. Arsenic (As), which exceeds 15 to 25 times higher than a standard value thereof, lead (Pb), which exceeds two times higher than a standard value thereof, and cadmium (Cd) exceeding a standard value thereof, are detected in a soil around a yard of the mineral tailings. Arsenic (As), which exceeds 20 times higher than the standard value thereof, is detected in a rice paddy or a dry field in the contact with the yard of the mineral tailings. In Samkwang mine, the main cause of the high concentration of Arsenic (As) is determined as mineral tailings, and Arsenic (As) is significantly spread into a surrounding area.

Embodiment 1: On-Site Evaluation of Final Equilibrium pH from Soil Collected from Sandong Mine A soil collected from Sangdong mine located in Yeongwol-gun, Kangwan-do, Korea was sieved in 60 meshes, and 10 g of the sieved soil was put into a paper cup. In addition, 50 ml of distilled water was put into the paper cup and neglected. If necessity, a slight amount of distilled water was additionally added into the paper cup to make the soil in a paste state and the pH of the soil in the paste state was measured. In this case, the paste pH was 8.9. The initial pH was set to 1, 2, 3, 4, 5, 6, 7, 8, 9, and 10, and the final equilibrium pH was evaluated by applying the initial pH to Equation 1. The final equilibrium pH according to each initial pH in the range of 1 to 10 was shown in following table 1.

Embodiment 2: On-Site Evaluation of Final Equilibrium pH from Soil Collected from Yeonhwa Mine The second embodiment is applied to Equation 1 in the same manner as that of the first embodiment except for a soil collected from Yeonhwa mine located in Samcheok-si, Kangwon-do, Korea to evaluate the final equilibrium pH. In this case, the paste pH was 7.8.

Embodiment 3: On-Site Evaluation of Final Equilibrium pH from Soil Collected from Janggun Mine The third embodiment is applied to Equation 1 in the same manner as that of the first embodiment except for a soil collected from Janggun mine located in Bonghwa-gun, Kyeonsangbuk-do, Korea to evaluate the final equilibrium pH. In this case, the paste pH was 7.1.

Embodiment 4: Second On-Site Evaluation of Final Equilibrium pH from Soil Collected from Janggun Mine The fourth embodiment is applied to Equation 1 in the same manner as that of the first embodiment except for a soil collected from Janggum mine located in Bonghwa-gun, Kyeonsangbuk-do, Korea to evaluate the final equilibrium pH. In this case, the paste pH was 7.8.

Embodiment 5: On-Site Evaluation of Final Equilibrium pH from Soil Collected from Samkwang Mine The fifth embodiment is applied to Equation 1 in the same manner as that of the first embodiment except for a soil collected from Sankwang mine located in Cheongyang-gun, Chungcheongnam-do, Korea to evaluate the final equilibrium pH. In this case, the paste pH was 9.1.

Embodiment 6: On-Site Evaluation of Final Equilibrium pH from Soil Collected from Deokchon Mine The sixth embodiment is applied to Equation 1 in the same manner as that of the first embodiment except for a soil collected from Deokchon mine located in Hapcheon-gun, Kyeongsangnam-do, Korea to evaluate the final equilibrium pH. In this case, the paste pH was 7.8.

Embodiment 7: On-Site Evaluation of Final Equilibrium pH from Soil Collected from Sannae Mine The seventh embodiment is applied to Equation 1 in the same manner as that of the first embodiment except for a soil collected from Sannae mine located in Milyang-gun, Kyeongsangnam-do, Korea to evaluate the final equilibrium pH. In this case, the paste pH was 7.8.

Embodiment 8: On-Site Evaluation of Final Equilibrium pH from Soil Collected from Yeosu Mine The eighth embodiment is applied to Equation 1 in the same manner as that of the first embodiment except for a soil collected from Yeosu mine located in Yeoju-gun, Kyeonggi-do, Korea to evaluate the final equilibrium pH. In this case, the paste pH was 6.1.

Embodiment 9: On-Site Evaluation of Final Equilibrium pH from Soil Collected from Dokseong Mine The ninth embodiment is applied to Equation 1 in the same manner as that of the first embodiment except for a soil collected from Dokseong mine located in Yongin-si, Kyeonggi-do, Korea to evaluate the final equilibrium pH. In this case, the paste pH was 5.9.

Embodiment 10: On-Site Evaluation of Final Equilibrium pH from Soil Collected from Yaro Mine The tenth embodiment is applied to Equation 1 in the same manner as that of the first embodiment except for a soil collected from Yaro mine located in Hapcheon-gun, Kyeongsangnam-do, Korea to evaluate the final equilibrium pH. In this case, the paste pH was 5.7.

Embodiment 11: On-Site Evaluation of Final Equilibrium pH from Soil Collected from Teachang Mine The eleventh embodiment is applied to Equation 1 in the same manner as that of the first embodiment except for a soil collected from Teachang mine located in Chungju-si, Chungcheonbuk-do, Korea to evaluate the final equilibrium pH. In this case, the paste pH was 4.7.

Embodiment 12: On-Site Evaluation of Final Equilibrium pH from Soil Collected from Backwol Mine The twelfth embodiment is applied to Equation 1 in the same manner as that of the first embodiment except for a soil collected from Backwol mine located in Changwon-si, Kyeongsangnam-do, Korea to evaluate the final equilibrium pH. In this case, the paste pH was 4.3.

Embodiment 13: On-Site Evaluation of Final Equilibrium pH from Soil Collected from Gumgae Mine The thirteenth embodiment is applied to Equation 1 in the same manner as that of the first embodiment except for a soil collected from Gumgae mine located in Yanpyeong-gun, Kyeonggi-do, Korea to evaluate the final equilibrium pH. In this case, the paste pH was 3.9.

Embodiment 14: On-Site Evaluation of Final Equilibrium pH from Soil Collected from Munmyeong Mine The fourteenth embodiment is applied to Equation 1 in the same manner as that of the first embodiment except for a soil collected from Munmyeong mine located in Yeongduk-gun, Kyeongsangbuk-do, Korea to evaluate the final equilibrium pH. In this case, the paste pH was 3.4.

Embodiment 15: On-Site Evaluation of Final Equilibrium pH from Soil Collected from Shinlim Mine The fifteenth embodiment is applied to Equation 1 in the same manner as that of the first embodiment except for a soil collected from Shinlim mine located in Wonju-si, Kangwon-do, Korea to evaluate the final equilibrium pH. In this case, the paste pH was 3.3.

Embodiment 16: On-Site Evaluation of Final Equilibrium pH from Soil Collected from Gakhee Mine The sixteenth embodiment is applied to Equation 1 in the same manner as that of the first embodiment except for a soil collected from Gakhee mine located in Bonghwa-gun, Kyeongsangbuk-do, Korea to evaluate the final equilibrium pH. In this case, the paste pH was 3.2.

Embodiment 17: On-Site Evaluation of Final Equilibrium pH from Soil Collected from Daeyang Mine The seventeenth embodiment is applied to Equation 1 in the same manner as that of the first embodiment except for a soil collected from Daeyang mine located in Jecheon-si, Chungcheongbuk-do, Korea to evaluate the final equilibrium pH. In this case, the paste pH was 3.0.

Embodiment 18: On-Site Evaluation of Final Equilibrium pH from Soil Collected from Ilwall Mine The eighteenth embodiment is applied to Equation 1 in the same manner as that of the first embodiment except for a soil collected from Ilwall mine located in Yeongyang-gun, Kyeongsangbuk-do, Korea to evaluate the final equilibrium pH. In this case, the paste pH was 2.6.

Embodiment 19: On-Site Evaluation of Final Equilibrium pH from Soil Collected from Jangja Mine The nineteenth embodiment is applied to Equation 1 in the same manner as that of the first embodiment except for a soil collected from Jangja mine located in Cheongsong-gun, Kyeongsangbuk-do, Korea to evaluate the final equilibrium pH. In this case, the paste pH was 2.1.

Following table 1 shows the final equilibrium pH calculated through Equation 1 with respect to mines according to the first to nineteenth embodiments, from which a soil is collected, the paste pH, and each initial pH.

TABLE 1

| Example | Mine name | Paste pH | Initial pH | | | | | | | | | |
|---|---|---|---|---|---|---|---|---|---|---|---|---|
| | | | 1 | 2 | 3 | 4 | 5 | 6 | 7 | 8 | 9 | 10 |
| Embodiment 1 | Sangdong | 8.9 | 3.6 | 6.0 | 7.1 | 7.6 | 8.0 | 8.2 | 8.3 | 8.4 | 8.5 | 8.6 |
| Embodiment 2 | Yeonhwa | 7.8 | 3.2 | 5.3 | 6.3 | 6.7 | 7.0 | 7.2 | 7.3 | 7.4 | 7.5 | 7.5 |
| Embodiment 3 | Janggun | 7.1 | 3.0 | 4.9 | 5.7 | 6.2 | 6.4 | 6.6 | 6.7 | 6.8 | 6.8 | 6.9 |
| Embodiment 4 | Janggun | 7.8 | 3.2 | 5.3 | 6.3 | 6.7 | 7.0 | 7.2 | 7.3 | 7.4 | 7.5 | 7.5 |
| Embodiment 5 | Samkwang | 9.1 | 3.7 | 6.1 | 7.2 | 7.8 | 8.1 | 8.4 | 8.5 | 8.6 | 8.7 | 8.8 |
| Embodiment 6 | Deokchon | 7.8 | 3.2 | 5.3 | 6.3 | 6.7 | 7.0 | 7.2 | 7.3 | 7.4 | 7.5 | 7.5 |
| Embodiment 7 | Sannae | 7.8 | 3.2 | 5.3 | 6.3 | 6.7 | 7.0 | 7.2 | 7.3 | 7.4 | 7.5 | 7.5 |
| Embodiment 8 | Yeosu | 6.1 | 2.6 | 4.3 | 5.0 | 5.4 | 5.6 | 5.7 | 5.8 | 5.9 | 5.9 | 5.9 |
| Embodiment 9 | Dokseong | 5.9 | 2.5 | 4.2 | 4.8 | 5.2 | 5.4 | 5.5 | 5.6 | 5.7 | 5.7 | 5.7 |
| Embodiment 10 | Yaro | 5.7 | 2.5 | 4.0 | 4.7 | 5.0 | 5.2 | 5.3 | 5.4 | 5.5 | 5.5 | 5.6 |
| Embodiment 11 | Taechang | 4.7 | 2.1 | 3.4 | 3.9 | 4.2 | 4.3 | 4.4 | 4.5 | 4.5 | 4.6 | 4.6 |
| Embodiment 12 | Backwol | 4.3 | 1.9 | 3.1 | 3.6 | 3.9 | 4.0 | 4.1 | 4.1 | 4.2 | 4.2 | 4.2 |
| Embodiment 13 | Gumgae | 3.9 | 1.8 | 2.9 | 3.3 | 3.5 | 3.6 | 3.7 | 3.8 | 3.8 | 3.8 | 3.8 |
| Embodiment 14 | Munmyeong | 3.4 | 1.6 | 2.6 | 2.9 | 3.1 | 3.2 | 3.2 | 3.3 | 3.3 | 3.3 | 3.3 |
| Embodiment 15 | Shinlim | 3.3 | 1.6 | 2.5 | 2.8 | 3.0 | 3.1 | 3.2 | 3.2 | 3.2 | 3.2 | 3.2 |
| Embodiment 16 | Gakhee | 3.2 | 1.5 | 2.4 | 2.8 | 2.9 | 3.0 | 3.1 | 3.1 | 3.1 | 3.1 | 3.1 |
| Embodiment 17 | Daeyang | 3.0 | 1.5 | 2.3 | 2.6 | 2.7 | 2.8 | 2.9 | 2.9 | 2.9 | 2.9 | 2.9 |
| Embodiment 18 | Ilwall | 2.6 | 1.3 | 2.0 | 2.3 | 2.4 | 2.5 | 2.5 | 2.5 | 2.5 | 2.6 | 2.6 |
| Embodiment 19 | Jangja | 2.1 | 1.1 | 1.7 | 1.9 | 2.0 | 2.0 | 2.0 | 2.0 | 2.1 | 2.1 | 2.1 |

Table 2 shows the analysis of the metal component and the specific gravity of a contaminated soil collected from mines to be investigated according to the first to nineteenth embodiments.

TABLE 2

| Embodiment | Metal component | Specific gravity |
|---|---|---|
| Embodiment 1 | W | 2.91 |
| Embodiment 2 | Pb, Zn | 3.42 |
| Embodiment 3 | Cu, Pb, Zn, Mn | 3.42 |
| Embodiment 4 | Cu, Pb, Zn, Mn | 3.59 |
| Embodiment 5 | Au, Ag, Pb, Zn | 2.69 |
| Embodiment 6 | Au, Ag | 2.85 |
| Embodiment 7 | W, Mo | 2.81 |
| Embodiment 8 | Au, Ag | 2.65 |

TABLE 2-continued

| Embodiment | Metal component | Specific gravity |
|---|---|---|
| Embodiment 9 | Au | 2.67 |
| Embodiment 10 | Au, Ag, Pb, Zn | 3.00 |
| Embodiment 11 | Au, Ag | 2.68 |
| Embodiment 12 | Zn | 2.78 |
| Embodiment 13 | Au, Ag, Cu, Pb, Zn | 2.67 |
| Embodiment 14 | Au, Ag | 2.76 |
| Embodiment 15 | Ag | 2.85 |
| Embodiment 16 | Au, Ag, Pb | 2.61 |
| Embodiment 17 | W | 3.65 |
| Embodiment 18 | Au, Ag, Cu | 3.33 |
| Embodiment 19 | Ag, Zn, Cu, Pb | 2.85 |

Figure 2:
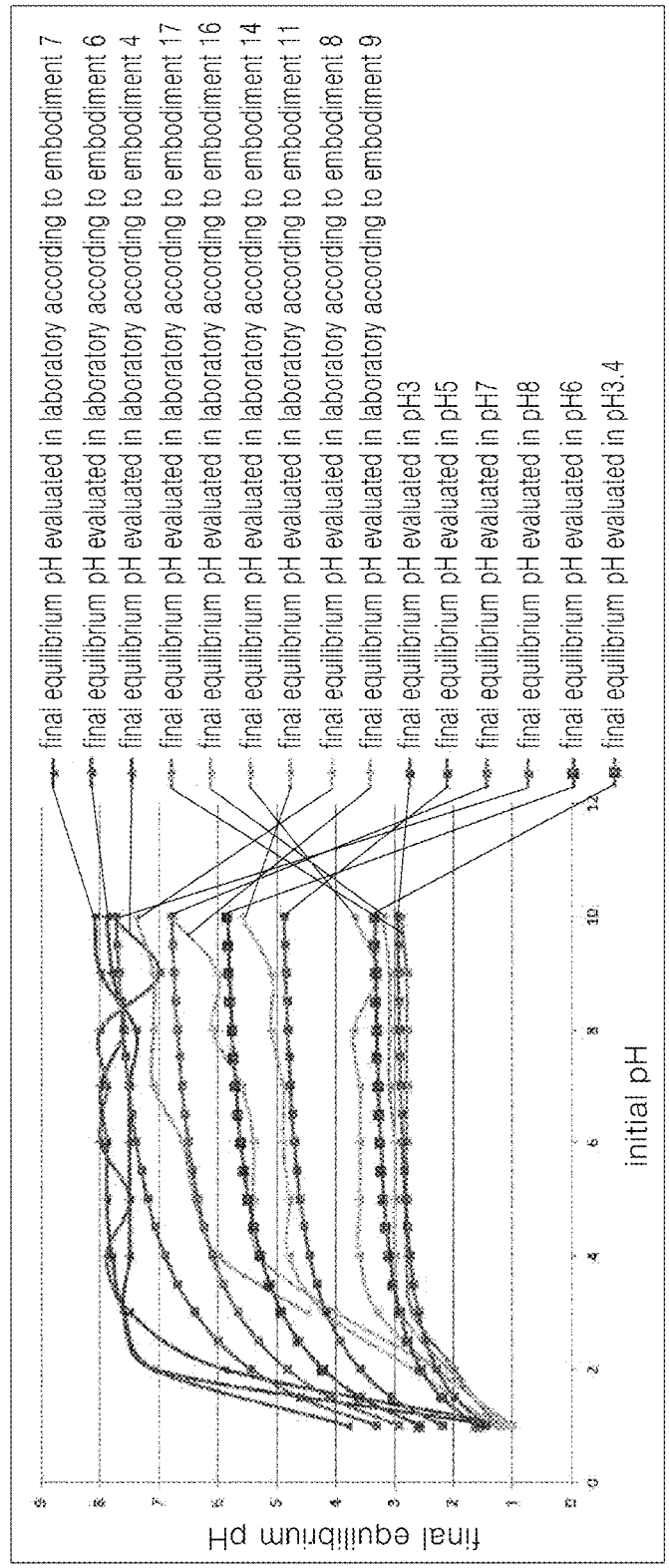
FIG. 2 is a graph showing the final equilibrium pH of the first to nineteenth embodiments measured in the method of evaluating the final equilibrium pH of the contaminated soil on site by using the paste pH and the result of the final equilibrium pH measured in a laboratory according to each embodiment.

Experimental Example 1: Analysis of Final Equilibrium pH Measured on Site and Final Equilibrium pH Evaluated in Laboratory The results of the final equilibrium pH evaluated through Equation 1 according to the first to nineteenth embodiments in the method of evaluating the final equilibrium pH of the contaminated soil on site by using the paste pH according to the present invention, and the results of the final equilibrium pH measured in a laboratory according to each embodiment are shown in table 3 and FIG. 2.

TABLE 3

| | Initial pH | | | | | | | | | |
|---|---|---|---|---|---|---|---|---|---|---|
| | 1 | 2 | 3 | 4 | 5 | 6 | 7 | 8 | 9 | 10 |
| Calculated value of Embodiment 1 | 3.6 | 6.0 | 7.1 | 7.6 | 8.0 | 8.2 | 8.3 | 8.4 | 8.5 | 8.6 |
| Measured final equilibrium pH | 3.8 | — | 8.0 | 8.2 | 7.6 | 7.8 | 7.7 | 7.9 | 7.7 | 7.9 |
| Calculated value of Embodiment 2 | 3.2 | 5.3 | 6.3 | 6.7 | 7.0 | 7.2 | 7.3 | 7.4 | 7.5 | 7.5 |
| Measured final equilibrium pH | 1.1 | 2.3 | 7.7 | 7.6 | 7.7 | 7.8 | 7.7 | 7.7 | 7.9 | 7.7 |

TABLE 3-continued

|  | Initial pH | | | | | | | | | |
|---|---|---|---|---|---|---|---|---|---|---|
|  | 1 | 2 | 3 | 4 | 5 | 6 | 7 | 8 | 9 | 10 |
| Calculated value of Embodiment 3 | 3.0 | 4.9 | 5.7 | 6.2 | 6.4 | 6.6 | 6.7 | 6.8 | 6.8 | 6.9 |
| Measured final equilibrium pH | 1.9 | 6.9 | 7.2 | 7.6 | 7.6 | 7.8 | 7.8 | 7.8 | 7.4 | 6.3 |
| Calculated value of Embodiment 4 | 3.2 | 5.3 | 6.3 | 6.7 | 7.0 | 7.2 | 7.3 | 7.4 | 7.5 | 7.5 |
| Measured final equilibrium pH | 3.8 | 7.1 | 7.6 | 7.9 | 7.5 | 8.0 | 7.9 | 8.0 | 7.0 | 7.8 |
| Calculated value of Embodiment 5 | 3.7 | 6.1 | 7.2 | 7.8 | 8.1 | 8.4 | 8.5 | 8.6 | 8.7 | 8.8 |
| Measured final equilibrium pH | 5.3 | 7.8 | 9.1 | 9.5 | 8.2 | 8.2 | 8.2 | 8.2 | 8.3 | 8.6 |
| Calculated value of Embodiment 6 | 3.2 | 5.3 | 6.3 | 6.7 | 7.0 | 7.2 | 7.3 | 7.4 | 7.5 | 7.5 |
| Measured final equilibrium pH | 1.0 | 5.9 | 7.5 | 7.8 | 7.9 | 7.9 | 8.0 | 7.6 | 7.8 | 7.9 |
| Calculated value of Embodiment 7 | 3.2 | 5.3 | 6.3 | 6.7 | 7.0 | 7.2 | 7.3 | 7.4 | 7.5 | 7.5 |
| Measured final equilibrium pH | 1.3 | 7.1 | 7.6 | 7.5 | 7.5 | 7.5 | 7.5 | 7.4 | 8.0 | 8.1 |
| Calculated value of Embodiment 8 | 2.6 | 4.3 | 5.0 | 5.4 | 5.6 | 5.7 | 5.8 | 5.9 | 5.9 | 5.9 |
| Measured final equilibrium pH | 1.1 | — | 4.5 | 6.0 | 6.4 | 6.6 | 7.1 | 7.1 | 7.1 | 7.4 |
| Calculated value of Embodiment 9 | 2.5 | 4.2 | 4.8 | 5.2 | 5.4 | 5.5 | 5.6 | 5.7 | 5.7 | 5.7 |
| Measured final equilibrium pH | 1.1 | 2.3 | 4.0 | 5.3 | 5.4 | 5.4 | 5.6 | 6.1 | 6.0 | 6.8 |
| Calculated value of Embodiment 10 | 2.5 | 4.0 | 4.7 | 5.0 | 5.2 | 5.3 | 5.4 | 5.5 | 5.5 | 5.6 |
| Measured final equilibrium pH | 1.2 | 5.4 | 6.3 | 6.3 | 6.3 | 6.3 | 6.4 | 6.3 | 6.9 | 6.9 |
| Calculated value of Embodiment 11 | 2.1 | 3.4 | 3.9 | 4.2 | 4.3 | 4.4 | 4.5 | 4.5 | 4.6 | 4.6 |
| Measured final equilibrium pH | 1.3 | 2.7 | 4.2 | 4.8 | 4.8 | 4.9 | 4.9 | 5.1 | 5.1 | 5.6 |
| Calculated value of Embodiment 12 | 1.9 | 3.1 | 3.6 | 3.9 | 4.0 | 4.1 | 4.1 | 4.2 | 4.2 | 4.2 |
| Measured final equilibrium pH | 1.0 | 2.8 | 3.9 | 3.9 | 4.3 | 4.3 | 4.1 | 4.3 | 3.9 | 4.3 |
| Calculated value of Embodiment 13 | 1.8 | 2.9 | 3.3 | 3.5 | 3.6 | 3.7 | 3.8 | 3.8 | 3.8 | 3.8 |
| Measured final equilibrium pH | 1.2 | 2.1 | 3.1 | 3.7 | 3.9 | 4.0 | 4.0 | 4.2 | 4.2 | 4.7 |
| Calculated value of Embodiment 14 | 1.6 | 2.6 | 2.9 | 3.1 | 3.2 | 3.2 | 3.3 | 3.3 | 3.3 | 3.3 |
| Measured final equilibrium pH | 1.0 | 2.3 | 3.3 | 3.6 | 3.6 | 3.6 | 3.6 | 3.7 | 3.3 | 3.7 |
| Calculated value of Embodiment 15 | 1.6 | 2.5 | 2.8 | 3.0 | 3.1 | 3.2 | 3.2 | 3.2 | 3.2 | 3.2 |
| Measured final equilibrium pH | 1.4 | 2.5 | 3.3 | 3.4 | 3.4 | 3.4 | 3.4 | 3.4 | 3.4 | 3.4 |
| Calculated value of Embodiment 16 | 1.5 | 2.4 | 2.8 | 2.9 | 3.0 | 3.1 | 3.1 | 3.1 | 3.1 | 3.1 |
| Measured final equilibrium pH | 1.2 | 2.1 | 2.9 | 3.0 | 3.0 | 3.0 | 3.1 | 3.1 | 3.1 | 3.2 |
| Calculated value of Embodiment 17 | 1.5 | 2.3 | 2.6 | 2.7 | 2.8 | 2.9 | 2.9 | 2.9 | 2.9 | 2.9 |
| Measured final equilibrium pH | 1.3 | 2.0 | 2.7 | 2.8 | 2.8 | 2.8 | 2.8 | 2.8 | 2.8 | 2.9 |
| Calculated value of Embodiment 18 | 1.3 | 2.0 | 2.3 | 2.4 | 2.5 | 2.5 | 2.5 | 2.5 | 2.6 | 2.6 |
| Measured final equilibrium pH | 1.0 | 2.1 | 2.6 | 2.8 | 2.8 | 2.8 | 2.8 | 2.9 | 2.8 | 2.9 |
| Calculated value of Embodiment 19 | 1.1 | 1.7 | 1.9 | 2.0 | 2.0 | 2.0 | 2.0 | 2.1 | 2.1 | 2.1 |
| Measured final equilibrium pH | 1.0 | 2.1 | 2.2 | 2.2 | 2.2 | 2.2 | 2.2 | 2.4 | 2.2 | 2.2 |

It can be recognized from table 3 that the final equilibrium pH calculated in the method of evaluating the final equilibrium pH of the contaminated soil on site by using the paste pH according to the present invention is significantly approximate to the final equilibrium pH measured in the laboratory. Accordingly, the final equilibrium pH value can be simply obtained in real time on site.

Until now, the method of evaluating the final equilibrium pH of the contaminated soil on site by using the paste pH according to the embodiment of the present invention has been described in detail, it is obvious that various modifications may be made by those skilled in the art without departing from the scope of the present invention.

As described above, although various examples have been illustrated and described, the present disclosure is not limited to the above-mentioned examples and various modifications can be made by those skilled in the art without departing from the scope of the appended claims. In addition, these modified examples should not be appreciated separately from technical spirits or prospects.

Therefore, it should be understood that the present invention is not limited to the embodiments described above. The scope of the present invention will be limited by the appended claims. In addition, it will also be apparent to those skilled in the art that variations or modifications from the appended claims and the equivalent concept of the claims are included in the scope of the present invention.

What is claimed is:

1. A method of evaluating a final equilibrium pH of a contaminated soil on site by using a paste pH, the method comprising:
    measuring the paste pH by adding a solution to the contaminated soil to make it in a paste state; and
    evaluating the final equilibrium pH according to an initial pH comprising a pH of a raindrop, underground water, or ore industry sewage by applying the paste pH to Equation 1, $$\text{Final equilibrium pH} = (\text{paste pH} + 1) \times \exp\left(-\frac{1}{\text{initial pH}}\right) - \exp\left(-\frac{1(\text{paste pH} + 1)}{\text{initial pH}}\right), \quad \text{Equation 1}$$

in which the initial pH is a predetermined integer in a range of 4 to 10.

2. The method of claim 1, wherein the contaminated soil comprises at least one of a mineral tailing and a waste rock.

3. The method of claim 1, wherein the solution comprises distilled water, or water.

* * * * *